(12) United States Patent
Ågerup

(10) Patent No.: US 7,278,985 B2
(45) Date of Patent: Oct. 9, 2007

(54) MEDICAL PUMP

(75) Inventor: Bengt Ågerup, Paris (FR)

(73) Assignee: Q Med AB, Uppsala (SE)

( * ) Notice: Subject to any disclaimer, the term of this patent is extended or adjusted under 35 U.S.C. 154(b) by 315 days.

(21) Appl. No.: 10/464,776

(22) Filed: Jun. 19, 2003

(65) Prior Publication Data

US 2004/0267201 A1    Dec. 30, 2004

(30) Foreign Application Priority Data

Jun. 18, 2003   (SE) .................................. 0301761

(51) Int. Cl.
*A61M 5/00*    (2006.01)
*A61M 5/315*   (2006.01)
*A61M 37/00*   (2006.01)

(52) U.S. Cl. .................. 604/191; 604/181; 604/221; 604/187; 604/89

(58) Field of Classification Search ............ 604/191, 604/89, 91, 181, 221, 218, 131, 134
See application file for complete search history.

(56) References Cited

U.S. PATENT DOCUMENTS

| 212,046 | A | * | 2/1879 | Palmer ................... 604/183 |
| 1,950,137 | A | * | 3/1934 | Dowe ...................... 604/30 |
| 4,643,723 | A | * | 2/1987 | Smit ........................ 604/207 |
| 4,664,128 | A | * | 5/1987 | Lee .......................... 600/566 |
| 5,178,300 | A | * | 1/1993 | Haviv et al. ............ 222/95 |
| 5,213,839 | A |   | 5/1993 | Awazu et al. |
| 5,222,497 | A |   | 6/1993 | Ono |
| 5,242,416 | A |   | 9/1993 | Hutson |
| 5,489,272 | A |   | 2/1996 | Wirtz |
| 5,496,284 | A |   | 3/1996 | Waldenburg ............ 604/191 |
| 5,702,366 | A |   | 12/1997 | Lichtenberg |
| 5,713,873 | A |   | 2/1998 | Jehle |
| 5,785,683 | A |   | 7/1998 | Szapiro et al. |
| 6,132,400 | A | * | 10/2000 | Waldenburg ............ 604/191 |

(Continued)

FOREIGN PATENT DOCUMENTS

EP          0845275         6/1998

(Continued)

OTHER PUBLICATIONS

Kalla: FASS.se, Karbasal, kram 400 g burk, med pump, Senaste revision Jan. 28, 1999, http://www.apoteket.se/is-bin/INTERSHOP.efinity/eCS/Store/sv/-/SEK/ApoViewPr... Dec. 11, 2003.

(Continued)

*Primary Examiner*—Kevin C. Sirmons
*Assistant Examiner*—Benjamin Huh
(74) *Attorney, Agent, or Firm*—Harness, Dickey & Pierce, P.L.C.

(57) ABSTRACT

A medical pump, comprising a reservoir having a fluid enclosing portion and a tubular element, the inside of which is arrangeable in fluid communication with the fluid enclosing portion for allowing fluid to pass into the tubular element. The fluid enclosing portion contains a volume of fluid sealed from communication with air and the fluid enclosing portion is adapted to reduce in volume essentially to the same extent as any volume of fluid transferred into the inside of the tubular element. The invention also relates to a method of delivering a medical fluid.

22 Claims, 7 Drawing Sheets

U.S. PATENT DOCUMENTS

| | | |
|---|---|---|
| 6,331,174 B1 | 12/2001 | Reinhard et al. |
| 2001/0039400 A1 | 11/2001 | Lubrecht |

FOREIGN PATENT DOCUMENTS

| | | |
|---|---|---|
| WO | WO 96/10430 | 4/1996 |
| WO | WO96/10430 | 4/1996 |
| WO | WO 01/74427 | 10/2001 |
| WO | WO 02/070053 | 9/2002 |

OTHER PUBLICATIONS

Kalla: FASS.se, Karbasal, kram 400g refillburk, Senaste revision Jan. 28, 1999, http://www.apoteket.se/is-bin/INTERSHOP.efinity/eCS/Store/sv/-SEK/ApoViewPr... Dec. 11, 2003.

Search Report.

* cited by examiner

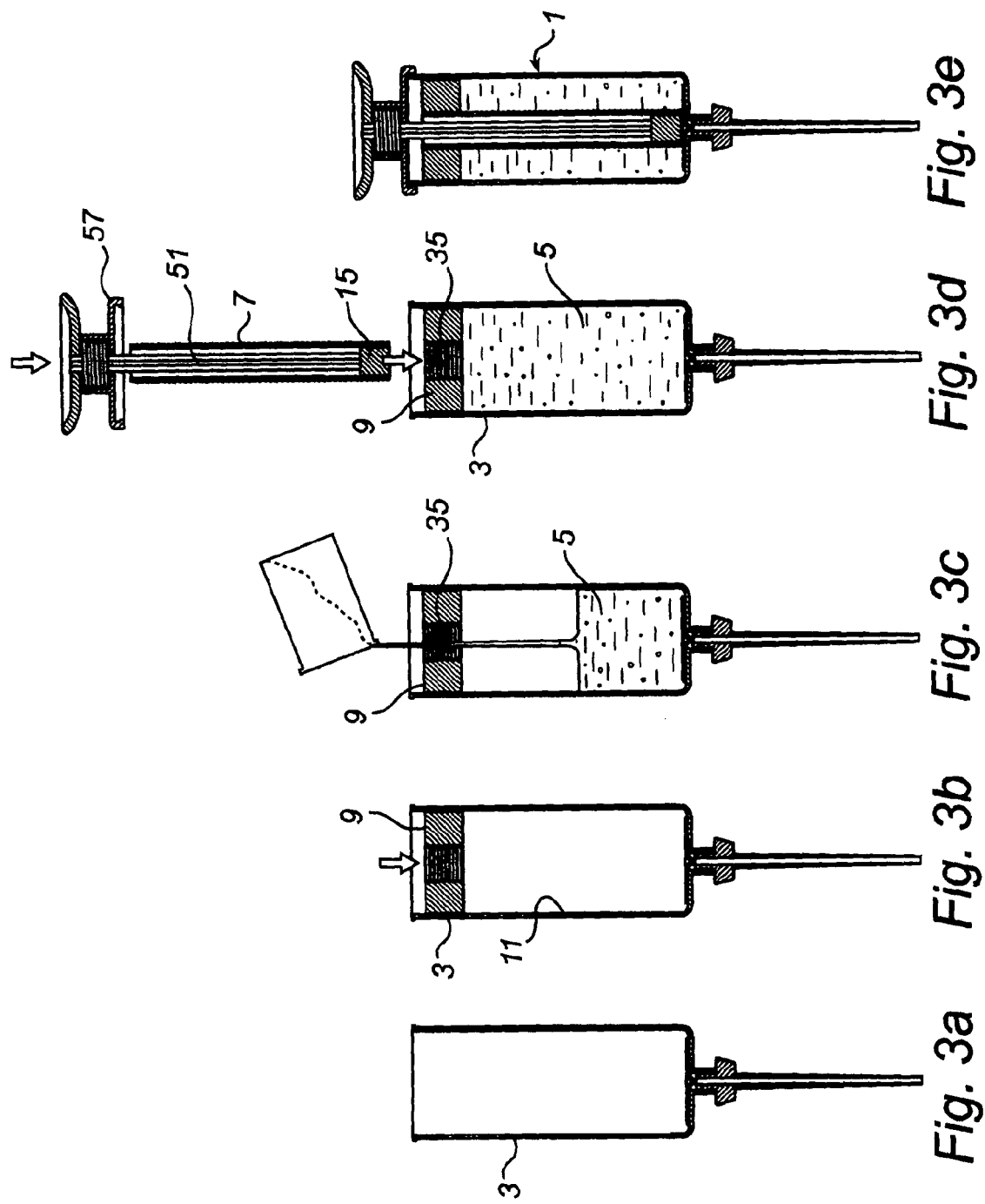

1
MEDICAL PUMP

This U.S. non-provisional application claims priority under 35 U.S.C. §119 to Swedish Patent Application No. 0301761-3, filed on Jun. 18, 2003, the contents of which are incorporated herein by reference in their entirety.

TECHNICAL FIELD

The present invention relates to a medical pump and to a method of delivering a medical fluid. In this application it is to be noted that the term fluid does not only encompass liquids but also gels.

BACKGROUND OF THE INVENTION

Syringes and other injection devices have different ranges of application. One of these is syringes for administration of fluids with a viscosity above 1000 mPa*s, such as a gel. For instance, a gel may be injected into the skin of a human being or an animal in order to obtain a volume augmentation of the skin. This application has been used in the esthetics industry for e.g. smoothing wrinkles and folds, shaping facial contours, lip sculpting, etc. Such gels are, for example, marketed by the applicant under the product trademarks Restylane and Perlane which are based on the so called NASHA-gel (Non-Animal Stabilized Hyaluronic Acid). Another application is for treating female urine incontinence wherein an injection of the gel is performed. The applicant markets such gel under the product trademark Zuidex (also a NASHA-gel). Another NASHA-gel product under the trademark Durolane is injected into the bone of a patient for treatment of e.g. knee osteoarthritis.

When a large quantity of fluid is to be delivered the syringe should have a large capacity, or should be refilled or changed several times during the administration. The large quantity generally makes the cross section of the syringe large and thereby the area of the plunger that transfers the applied pressure to the fluid will be large as well. The larger the diameter of the plunger is, the more pressure is needed to deliver the fluid out from the syringe. If the fluid is viscous, such as in the form of a gel, this particular problem with common syringes, containing a large quantity of fluid, is becoming even worse.

U.S. Pat. Nos. 5,496,284; 6,132,400 and WO 96/10430 describe syringes for administration of anesthetic. These syringes avoid the problem of a large plunger area, by providing a first smaller chamber having a plunger with a small area and a second chamber used as a reservoir, wherein the first chamber can be filled up with fluid from the second chamber. The small plunger area reduces the force that has to be applied during administration of the anesthetic.

While these prior art syringes facilitate the administration of an anesthetic in the form of a liquid having low viscosity, they are unsuitable for the administration of relatively viscous fluids, such as gels. A drawback of these prior art syringes is that the fluid contained within the reservoir stands in communication with air. The air is introduced when fluid is drawn into the delivery chamber during proximal movement of the plunger. If a viscous fluid is mixed with air, there is a risk that the air will be entrapped within the fluid and by that administrated into the body of a human or animal being. Another problem by mixing the fluid with air is the contamination that may defect the fluid.

SUMMARY OF THE INVENTION

An object of the invention is to provide a medical pump which is suitable for the administration of a relatively viscous fluid, in particular for a fluid having a viscosity of at least 1000 mPa*s, such as a gel, e.g. of the product types mentioned under the Background section of this description.

Another object of the invention is to provide a medical pump that contains a fluid prevented from mixing with air, and thereby reducing the risk of delivering a fluid containing entrapped air.

Another object of the invention is to provide a medical pump that prevents the fluid contained therein from mixing with air in order to reduce the risk of contamination of the fluid, and thereby reducing the risk of delivering defected fluid.

Yet another object of the invention is to provide a medical pump that has the capacity to contain an essentially large quantity of fluid and facilitate delivery of a viscous fluid, such as a gel, with application of a reduced force.

Additionally, an object of the invention is to provide a method of delivering a medical fluid, such as a viscous fluid, in particular a gel.

These and other objects, which will become apparent in the following description, are achieved by means of a medical pump and a method having the features defined in the appended claims.

According to a first aspect of the invention, a medical pump is provided, comprising a reservoir having a fluid enclosing portion;

a tubular element, the inside of which is arrangeable in fluid communication with the fluid enclosing portion for allowing fluid to pass into the tubular element;

a inner seal movable inside the tubular element between an advanced and a retracted position, wherein the inner seal is retractable from the advanced position to enable the fluid to be transferred from the fluid enclosing portion into an internal space defined by the tubular element and the retracted inner seal, and wherein the inner seal is advanceable from the retracted position for delivering out of the pump fluid present in said internal space;

wherein said fluid enclosing portion contains a volume of fluid sealed from communication with air and the fluid enclosing portion is adapted to reduce in volume essentially to the same extent as any volume of fluid transferred into said internal space of the tubular element.

The invention is based on the understanding that by providing a fluid inside a fluid enclosing portion which is capable of reducing in volume as the fluid is administered, it is possible to seal the fluid from communication with air. This is apparently a solution that goes against the identified prior art, where the reduced volume of fluid in the reservoir is replaced by introduction of air into the volume containing the fluid.

In this application the term reservoir is used to define the volume that is intended to at least partially contain a fluid. Further, the fluid enclosing portion is defined as the volume of fluid contained within the reservoir that is sealed from communication with air, wherein the inside of the tubular element, such as the volume of fluid contained within the internal space of the tubular element, is not part of the fluid enclosing portion. The delimitation surface of the fluid enclosing portion may at least partially be the same as the delimitation surface of the reservoir.

A particular advantage of the invention is that the fluid contained in the fluid enclosing portion is prevented from mixing with air. In particular, the risk of introducing air that may be entrapped within the fluid is reduced and thereby a medical pump is provided that facilitates a more safe and reliable delivering of fluid. Another advantage, with the medical pump containing a fluid prevented from mixing with air, is a reduced contamination of the fluid that reduce the risk of delivering defected fluid.

Another advantage of the invention is that a smaller volume of fluid to be delivered out from the medical pump is transferred from the fluid enclosing portion into said internal space, the force needed for the delivery is reduced compared to a medical pump where the fluid to be delivered is contained in one chamber comprising all the fluid. By transferring the fluid into said internal space, the area of the means used to force the fluid out from the medical pump may be reduced, and thereby the force needed for the delivery is reduced. This is particularly advantageous for gels, which generally have high viscosity.

The arrangeable fluid communication between the fluid enclosing portion and the inside of the tubular element is preferably made possible by the opening of a sealing, valve or other communication closing means.

In at least one embodiment the fluid communication between the internal space of the tubular element and the fluid enclosing portion is opened before the inner seal is retracted from the advanced position towards the retracted position. It may also be possible to open the fluid communication between the internal space of the tubular element and the fluid enclosing portion after the retraction of the inner seal or when the inner seal is partially retracted.

In at least one embodiment, the retraction of the inner seal creates a negative pressure inside the tubular element, wherein the negative pressure forces the fluid in the fluid enclosing portion to be transferred into the internal space of the tubular element. By enabling at least parts of the delimitation surface of the fluid enclosing portion to be movable or flexible, the volume of the fluid enclosing portion is reduced to the same extent as the volume transferred from the fluid enclosing portion into the internal space of the tubular element, without introducing air into the fluid enclosing portion. This implies that the remaining volume of the fluid enclosing portion is the difference between the volume of fluid contained within the fluid enclosing portion before transfer of fluid from the fluid enclosing portion and the volume of fluid transferred into the tubular element.

The invention is also based on the understanding that the volume of the fluid enclosing portion may be variable by providing a movable means within the reservoir, which means define a delimitation of the fluid enclosing portion.

In at least one embodiment, the fluid enclosing portion comprises an outer seal which is movable inside the reservoir and which defines a delimitation of the fluid contained in the fluid enclosing portion, the outer seal being arranged to at least partially move relative to the tubular element when the inner seal is retracted from said advanced position.

Preferably, the reservoir is formed as a tubular barrel and the outer seal, suitably cylindrical, is provided within the reservoir. The reservoir may be made of a transparent plastic material, such as polycarbonate, cyclo-olefin-copolymer (COC), polypropylene or other suitable material. The outer seal is arranged to create a sealing effect between the fluid contained within the reservoir and the environmental air, wherein the fluid is prevented from mixing with air. Preferably, the side of the outer seal opposite to the fluid enclosing portion stands in communication with air, in order to equalize the pressure surrounding the outer seal when the outer seal is moved due to transferring of fluid from the fluid enclosing portion into the internal space of the tubular element. Preferably, the outer seal is made of a flexible material, such as a rubber material, in particular butyl rubber. An alternative to rubber is thermoelastic plastics. The outer seal is provided to fit tight against the inner wall of the reservoir, in order to create the sealing effect. Advantageously, the outer circumferential surface of the outer seal is provided with grooves or channels for increased sealing effect.

Note that even if some embodiments including a moveable outer seal have been described above, it is to be understood that the fluid enclosing portion of the medical pump may be made of a flexible material that will collapse when the fluid is transferred out from the fluid enclosing portion into the internal space of the tubular element. This may be achieved by providing a fluid enclosing portion formed as a flexible sealed portion, such as a plastic bag. By collapsing the fluid enclosing portion, the volume of the fluid enclosing portion is reduced to the same extant as the volume transferred out from the fluid enclosing portion, wherein the fluid in the fluid enclosing portion is prevented from mixing with air.

As described above, the tubular element is provided with a movable inner seal that abuts against the inner wall of the tubular element in order to provide a sealing effect. Preferably, the inner seal is made of a flexible material, such as a rubber material, in particular butyl rubber, or some other suitable material such as thermoelastic plastics. Advantageously, the inner seal has an outer cylindrical surface which is provided with grooves or channels for increased sealing effect. The inner seal creates a negative pressure inside the tubular element when retracted from the advanced position towards the retracted position, which negative pressure creates a suction force that, after opening of the fluid communication between the reservoir and the internal space of the tubular element, pulls the fluid from the fluid enclosing portion into the internal space of the tubular element. The force created by the negative pressure is also applied to the outer seal, wherein the outer seal moves within the reservoir essentially the same distance as the movement of the fluid surface within the reservoir. Thereby, the outer seal is moved a distance corresponding to the volume transferred out from the fluid enclosing portion into the internal space of the tubular element. The movement of the outer seal makes it possible to reduce the volume of fluid in the reservoir without introducing air in the enclosed volume containing the fluid.

In at least one embodiment, the tubular element is located inside the reservoir, wherein the outer seal extends from an inner surface of the reservoir to an outer surface of the tubular element. The tubular element preferably extends through a hole provided in the outer seal, wherein the outer seal is suitably arranged to fit snugly over the outer wall of the tubular element to provide a sealing effect between the outer seal and the outer wall of the tubular element. Advantageously, when assembled, the reservoir, the outer seal and the tubular element are arranged concentrically within one another along a common longitudinal axis.

It is to be noted that the tubular element and the reservoir may be separated, wherein the fluid communication between the fluid enclosing portion and the internal space of the tubular element preferably is arranged with a passage in between, which advantageously is opened and closed by a valve. It shall also be noted that the outer seal is still movable within the reservoir relative to the tubular element in such an embodiment.

In at least one embodiment, the tubular element is movable between an advanced administering position and a retracted filling position, wherein the outer seal is adapted to move relative to the tubular element when the tubular element is retracted from said administering position.

The term "filling position" is used to define the position of the tubular element at which it is possible to transfer fluid from the fluid enclosing portion into the internal space of the tubular element or the soon to be created internal space of the tubular element. Accordingly, at this filling position, the inner seal may be retracted to create the internal space of the tubular element and enable the fluid in the fluid enclosing portion to be transferred into the internal space of the tubular element. The term "administering position" is used to define the position where the internal space of the tubular element is sealed from fluid communication with the fluid contained within the fluid enclosing portion. At this administering position the inner space of the tubular element is arrangeable in fluid communication with an outlet region, provided on the medical pump for enabling delivery of the fluid out from the medical pump.

It is to be noted that the fluid communication between the reservoir and the internal space of the tubular element also may be established by use of a valve or other fluid communication closure means.

The movement of the tubular element from said advanced administering position towards the retracted filling position is, in at least one embodiment, established by mutually contacting surfaces of the inner seal and the tubular element that provide a first frictional force $F_1$, wherein the tubular element is adapted to be retracted from the administering position by application of a retracting force on the inner seal. Further, the tubular element may be adapted to be advanced from the filling position by application of an advancing force on the inner seal, wherein a frictional force, directed opposite to the frictional force $F_1$, is created between the mutually contacting surfaces of the inner seal and the tubular element. The frictional forces, established when the tubular element is advanced and retracted respectively, are preferably in the same range. But the forces may also be different from each other, the essential function of these embodiments being that the frictional forces are sufficient to cause the movement of the tubular element between the advanced and retracted position.

It is to be noted that in this application the term "mutually contacting surfaces" is used to define portions of surfaces that abuts against each other for creation of a sealing effect and/or a frictional force.

Further, it is to be noted that the opening and closing function of the fluid communication between the fluid enclosing portion and the internal space of the tubular element, by moving the tubular element, may be separated from the retraction and advancement function of the inner seal. This may be achieved by an arrangement comprising separated control means for these two features.

In at least one embodiment, mutually contacting surfaces of the tubular element and the outer seal provide a second frictional force $F_2$ against advancing movement of the tubular element towards its administering position, and wherein mutually contacting surfaces of the outer seal and the reservoir provide a third frictional force $F_3$ which is smaller than said second frictional force $F_2$, wherein the outer seal is advanced together with the tubular element during advancement of the tubular element towards its administering position.

Hereby, the outer seal preferably is arranged to at least partially follow the movement of the tubular element, when advanced from the retracted position towards the advanced administering position. When the outer seal is advanced at least partially together with the tubular element, a pressure is created within the fluid contained in the reservoir. When the created pressure and the frictional force $F_3$ together apply a force to the outer seal, that is essentially in the same order as the frictional force $F_2$, the advancing movement of the outer seal is discontinued and the tubular element starts to slide relatively to the outer seal. The at least partial movement of the outer seal is obtained by arranging a relation between the frictional forces where the frictional force $F_2$ is larger than the frictional force $F_3$.

It is obvious for a person skilled in the art that the medical pump may be arranged with an outer seal that retains the position relatively to the reservoir when the tubular element is advanced towards the advanced administering position. This is obtained by arranging a relation between the frictional forces where the frictional force $F_2$ is equal or smaller than the frictional force $F_3$.

By moving the outer seal at least partially together with the tubular element, the created pressure increase within the fluid contained in the fluid enclosing portion facilitates additional retraction of the inner seal, after delivery of fluid contained within the internal space of the tubular element, in order to transfer fluid into the internal space of the tubular element from the fluid enclosing portion.

In at least one embodiment, mutually contacting surfaces of the outer seal and the reservoir provide a third frictional force $F_3$, and wherein mutually contacting surfaces of the tubular element and the outer seal provide a fourth frictional force $F_4$ against retracting movement of the tubular element towards its filling position, said third frictional force $F_3$ being larger than said fourth frictional force $F_4$.

Herby, the outer seal retains its position relatively to the reservoir when the tubular element is moved from its advanced administering position towards the retracted filling position. By retaining its position relatively to the reservoir, when the tubular element is moved from the advanced administering position towards the filling position, the outer seal essentially keeps the same level as the fluid within the fluid enclosing portion.

Preferably, the medical pump is arranged with a relationship between the frictional forces that satisfy $F_1 > F_2 > F_3 > F_4$. The frictional force $F_1$ defines the frictional force created between the inner wall of the tubular element and the inner seal for both retracted and advanced movement of the inner seal. In order to enable the tubular element to be lifted from the advanced administering position towards the retracted filling position by the frictional force $F_1$ between the inner seal and the tubular element, while enabling the outer seal to remain in position relative to the reservoir and to allow movement relative to the tubular element, the relation between the frictional forces is $F_1 > F_3 > F_4$. Further, in order to enable the tubular element to be advanced from the retracted filling position towards the advanced administering position by the frictional force $F_1$ between the inner seal and the tubular element, while enabling the outer seal to at least partially follow the movement of the tubular element, the relationship between the frictional forces is $F_1 > F_2 > F_3$.

The mutually contacting surfaces of the tubular element, the outer seal and the reservoir may be provided with surfaces and materials in such way that the relation between the frictional forces may be obtained. In at least one embodiment, the difference between the frictional force $F_2$, against advancing movement of the tubular element towards its administering position, and the frictional force $F_4$, against retracting movement of the tubular element towards its administering position, is created by an uneven surface, such as protruding means, provided to the outer wall of the tubular element. This protruding means may be formed as splines, barbs or edges, preferably provided on a rubber coating arranged around the outer wall of the tubular element. As an alternative, the difference between the frictional forces $F_2$ and $F_4$ may be established by providing the surface of the outer seal, which abuts against the outer wall of the tubular element, in a similar way as described for the tubular element. Note that even though in some embodiments it may be preferred to dimension $F_2 > F_4$, these frictional forces may also be equal or even have the reverse relationship.

Preferably, the reservoir comprises an abutment surface provided with an outlet region for fluid delivery out of the pump, wherein, in said administering position, an end portion of the tubular element abuts said abutment surface in such a manner that said internal space of the tubular element is in communication with said outlet region.

The outlet region is preferably arranged in the geometrical axis of the tubular element, even if the essential feature is that the internal space of the tubular element, in said administering position, is in communication with said outlet region. Further, the tubular element and the outlet region are preferably provided in the geometrical axis of the reservoir.

The abutment surface provided in the reservoir may act as a stop for the advancement of the tubular element towards the advanced administering position. In this case the advanced administering position may thus be defined as the location of the tubular element when it abuts against the abutment surface. However, the level of advancement of the inner seal defines the amount of fluid to be delivered out from the medical pump, wherein the inner seal e.g. may be advanced only half the way relative to the abutment surface in order to deliver a less amount of fluid out from the medical pump.

Further, in at least one embodiment, the abutment surface is a sealing surface preventing fluid from flowing between the interior of the tubular element and the fluid enclosing portion when the tubular element is in said administering position. Preferably the abutment surface is formed as a separate piece of material provided at the bottom of the reservoir. The abutment surface is preferably made of a rubber material, such as such as butyl rubber, or other suitable material such as thermoelastic plastics. The abutment surface may be attached to the reservoir by form fit, gluing or other fastening methods, but it is also possible to provide the abutment surface as a unattached piece of material. It may also be possible to provide the abutment surface as an integrated portion of the reservoir.

The shape of the abutment surface may be provided in several ways, e.g. as a plane surface or a as tapered surface, wherein the essential features is the definition of the administering position and the sealing effect between the internal space of the tubular element and the fluid contained within the fluid enclosing portion.

In at least one embodiment, said sealing surface is configured as a non-return valve which allows fluid to flow out from the pump through said outlet region but which prevents external fluid to enter the pump through said outlet region. As an alternative, the non-return valve may be provided as a separate part not formed as a portion of the sealing surface. It is also possible to vary the location of the non-return valve along the outlet region of the medical pump, wherein the non-return valve does not have to be located in contact with the abutment surface.

Preferably, the non-return valve is formed as a slit in the sealing surface, wherein at least two flaps are provided, which are enabled to open when the fluid is intended to be transferred out of the medical pump. The opening of the non-return valve is established when the inner seal is moved towards the advanced position, wherein the fluid contained within the internal space of the tubular element forces the non-return valve to open. Thereby, a fluid communication between the internal space of the tubular element and the outlet region is opened.

A person skilled in the art realizes that the non-return valve effect can be achieved in several ways.

The retracted filling position of the tubular element may be determined by an end member of the reservoir preventing the further retraction of the tubular element. The end member, in at least one embodiment, is made up by a cover provided at the end of the reservoir opposite to the opening region of the medical pump. Additionally, the cover is preferably provided to act as a stop member for the retraction of the inner seal from the advanced position to the retracted position. In this embodiment, the retracted position of the inner seal may thus be defined as the location of the inner seal when it abuts against the cover. However, the level of retraction of the inner seal defines the amount of fluid to be transferred into the internal space of the tubular element, wherein the inner seal e.g. may be retracted only half the way relative to the cover in order to transfer a less amount of fluid into the internal space of the tubular element.

In at least one embodiment, the inner seal is connected to an elongate actuator movable inside the tubular element, which actuator being controllable from the outside of the reservoir. When the inner seal is retracted from the advanced position due to a retracting force acting on the actuator, the tubular element is retracted to its filling position due to friction against the inner seal. Further, the inner seal is adapted to overcome the friction and move relative to the tubular element when the tubular element is at its filling position and the actuator is subjected to a retraction force.

Further, when the inner seal is advanced from the retracted position due to an advancing force acting on the actuator, the tubular element is advanced to its administration position due to friction against the inner seal, and when the tubular element is at its administering position and the actuator is subjected to a continued advancing force, the inner seal is adapted to overcome the friction and move relative to the tubular element.

The actuator is preferably provided with a control means, located outside the reservoir, adapted for a one hand grip for application of the retracting and advancing force. The connection of the inner seal to the actuator is preferably established by form fitting, but other fastening methods are usable as well. The elongate actuator may comprise a shaft or bar arranged between the inner seal and the controller means. The shaft or bar preferably has a cross shaped cross-section in order to among other things create a suitable connection interface to the inner seal.

Preferably, a spring is provided and biased to exert a force on the elongate actuator in the longitudinal direction of the actuator. The spring may either be arranged to transfer a retracting force to the actuator for facilitating the retracted movement of the inner seal towards its retracted position or arranged to transfer an advancing force to the actuator for facilitating the advancing movement of the inner seal towards its advanced position. In a preferred embodiment, the spring is arranged to facilitate the retracted movement of the inner seal. The purpose of the spring is to make the movement of the inner seal easier by transferring a force to the actuator and make the movement of the inner seal more smooth and controlled.

Preferably, the medical pump is provided as a package in which the reservoir is pre-filled with a medical fluid, such as a gel, having a viscosity above 1000 mPa*s, preferably above 10 000 mPa*s, in particular between than 100 000 mPa*s and 1 000 000 mPa*s. The fluid may be introduced to the medical pump under sterilized conditions in order to avoid contamination of the fluid. In order to avoid introduction of air at the assembly moment, the medical pump is preferably assembled under vacuum conditions. As a mere exemplifying comparison, it may be noted that water has a viscosity of about 1 mPa*s.

Preferably, the medical pump is intended to be disposable for one-time use. The medical pump is advantageously provided with a safety sealing that keeps the inner seal and the tubular element at the advanced position until the safety seal is broken before use of the medical pump. The safety seal is provided for safe transportation and indicates that the medical pump is used for the first time. Preferably, the safety seal is arranged as a locking means that holds the elongate actuator at the retracted position until the safety seal is broken, wherein the actuator may be retracted for enabling fluid to be transferred from the fluid enclosing portion into the internal space of the tubular element. When the safety seal is unbroken, the fluid communication between the reservoir and the internal space is closed, wherein all the fluid remains in the reservoir.

According to an additional aspect of the invention, a method of delivering medical fluid is provided, comprising: providing a medical pump comprising a reservoir having a fluid enclosing portion and a tubular element, the inside of which is arrangeable in fluid communication with the fluid enclosing portion;

reducing the volume of the volume of the fluid enclosing portion by transferring a portion of said fluid from the fluid enclosing portion into an internal space of the tubular element, wherein the volume of the fluid enclosing portion is reduced with essentially the same volume as the volume of fluid transferred into the internal space of the tubular element; and delivering out from the pump the transferred fluid contained in the internal space of the tubular element.

For further delivering of fluid from the pump, the preceding steps described above may be repeated. This procedure may be repeated until essentially all the fluid contained within the fluid enclosing portion has been transferred into and delivered from the internal space of the tubular element.

Suitably, the medical pump is assembled by:

providing a reservoir comprising at least one open end;

introducing a medical fluid into the reservoir, wherein the medical fluid being delimited by the outer seal;

introducing a moveable outer seal via the open end into the inside of the reservoir, wherein the outer seal abuts with sealing effect against the inner wall of the reservoir; and establishing a fluid enclosing portion free from air by sealing the volume of medical fluid contained within the reservoir by introducing a sealed tubular element through a hole in the outer seal, wherein the outer wall of the tubular element abuts with sealing effect against the outer seal.

The fluid enclosing portion is defined by the outer wall of the tubular element, the outer seal and at least partially the inner wall of the reservoir. When the medical pump is assembled, all the fluid is retained within the fluid enclosing portion until the first time the fluid communication is opened between the internal space of the tubular element and the fluid enclosing portion.

The assembling of the medical pump is preferably executed in an environment free from air, such as a vacuum area. After the medical pump is assembled, the medical pump may be enclosed in a sterilized package or a similar arrangement. The medical pump is preferably disposable for one time use only.

The filling up of the reservoir with the medical fluid may either be executed before the introduction of the outer seal into the reservoir or after the introduction of the outer seal into the reservoir. When the medical fluid, the outer seal and the sealed tubular element are introduced into the reservoir, the fluid enclosing portion contained within the reservoir is essentially free from air and sealed from mixing with environmental air.

When the outer seal is introduced into the reservoir before the medical fluid, the tubular element is preferably introduced into the reservoir together with the elongate actuator and the cover. In the case of introducing the medical fluid before the outer seal, the outer seal is preferably introduced together with the sealed tubular element, the elongate actuator and the cover.

BRIEF DESCRIPTION OF THE DRAWINGS

By way of examples, embodiments of the invention will now be described with reference to the accompanying drawings in which:

FIG. 3a-3e show, in cross section, a method of assembling the medical pump in FIG. 1.

DETAILED DESCRIPTION OF THE DRAWINGS

Figure 1:
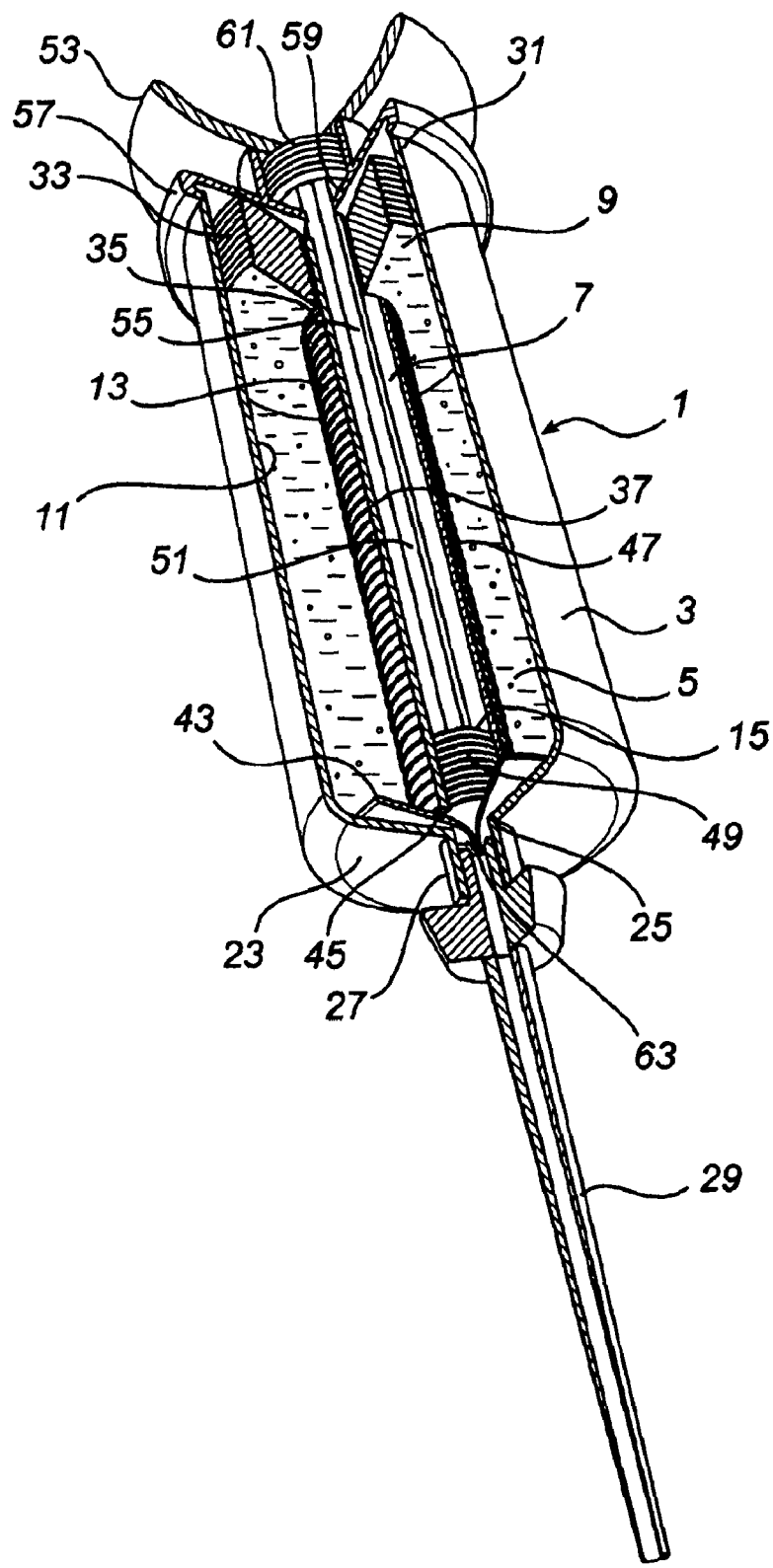
FIG. 1 shows a schematic perspective view, partially in cross section, of a medical pump comprising a medical fluid.

An embodiment of a medical pump according to the invention will now be described in more detail with reference to FIGS. 1-2e.

The medical pump 1 comprises a reservoir 3 intended to contain a fluid 5, a tubular element 7 arranged within the reservoir 3 and an outer seal 9 extending between the inner wall 11 of the reservoir and the outer wall 13 of the tubular element 7. The tubular element 7 is provided with an inner seal 15, movable inside the tubular element 7 between an advanced position (see FIGS. 1 and 2a) and a retracted position (see FIG. 2c). The inner seal 15 is retractable from the advanced position to the retracted position for enabling fluid 5 to be transferred from the portion of the reservoir 3 surrounding the tubular element 7 into an internal space 21 (see FIG. 2c) defined by the retracted inner seal 15 and the tubular element 7. Further the inner seal 15 is advanceable from the retracted position to the advanced position for delivering of fluid 5 out from the medical pump 1.

In the illustrated preferred embodiment the reservoir 3 is formed as a tubular barrel, and is preferably made of a transparent plastic material, such as polycarbonate or cyclo-olefin-copolymer. The reservoir 3 includes a front end 23 comprising an opening 25 through which the fluid 5 is intended to be delivered out from the medical pump 1 via a tubular end portion 27. The opening 25 is preferably placed in the geometrical axis of the reservoir 3 and the tubular end portion 27 may be adapted for receiving a needle 29 of generally standard type. Opposite to the front end 23 the reservoir has an open rear end 31.

The outer seal 9 is movably provided within the reservoir 3, intended to follow the level of fluid 5 contained inside the reservoir 3. The cylindrical outer surface of the outer seal 9 is in sealing contact with the inner wall 11 of the reservoir 3. Preferably, the outer seal 9 is made of a rubber material, such as butyl rubber, and said cylindrical outer surface of the outer seal 9 may be provided with grooves or channels 33 for increased sealing effect. Further, the outer seal 9 is arranged with a concentric hole 35 extending in the axial direction of the medical pump 1, which hole 35 is adapted to receive the tubular element 7 provided within the reservoir 3. The tubular element 7 extends through the hole 35 of the outer seal 9, and a sealing contact between the mutually contacting surfaces of the tubular element 7 and the outer seal 9 is established by letting the outer seal 9 fit snugly over the tubular element 7.

The circular inner seal 15 is provided inside the tubular element 7 and abuts against the inner wall 37 of the tubular element 7 to provide a sealing effect between the inner seal 15 and the tubular element 7. Hence, the outer seal 9 and the inner seal 15 define an enclosed volume inside the reservoir 3 intended to contain a fluid 5 essentially free from air.

Figure 2A:
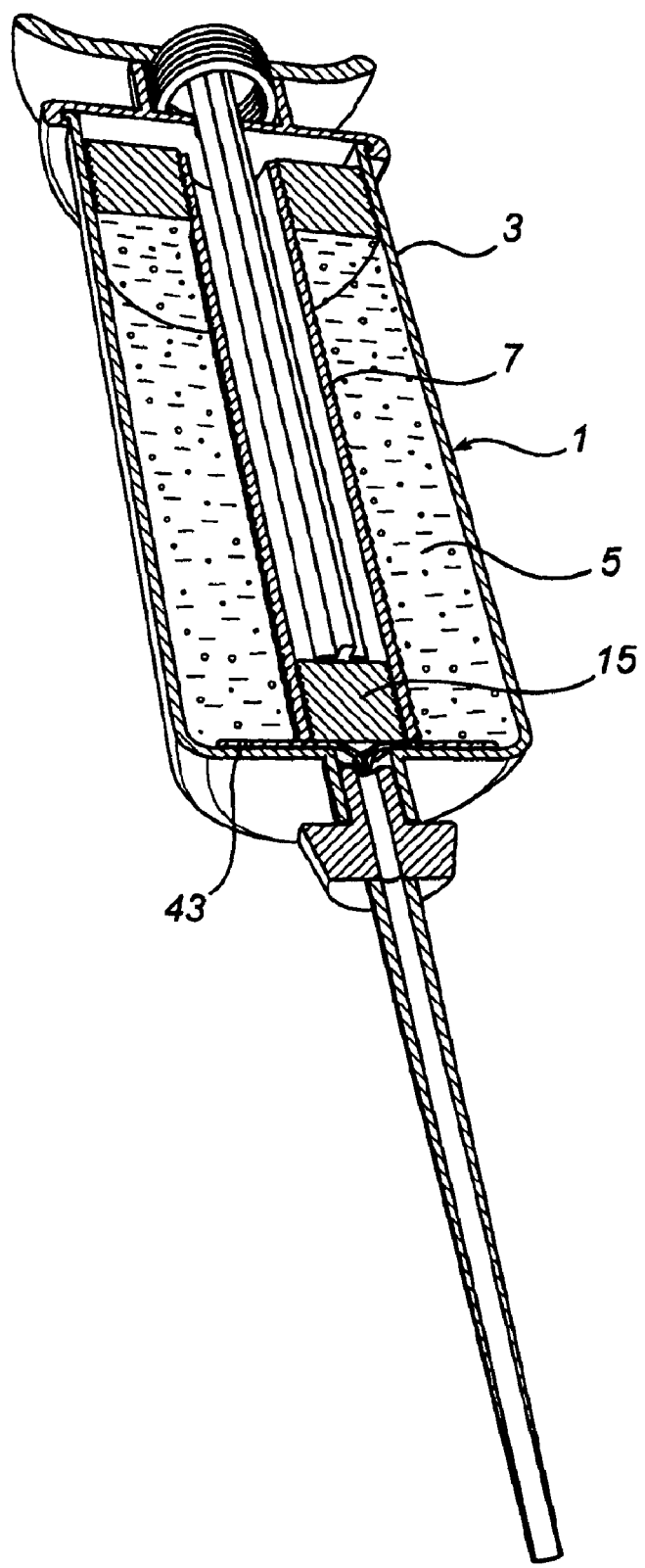
FIG. 2a-2e show, in cross section, a method of delivering fluid from the medical pump in FIG. 1.
Figure 2B:
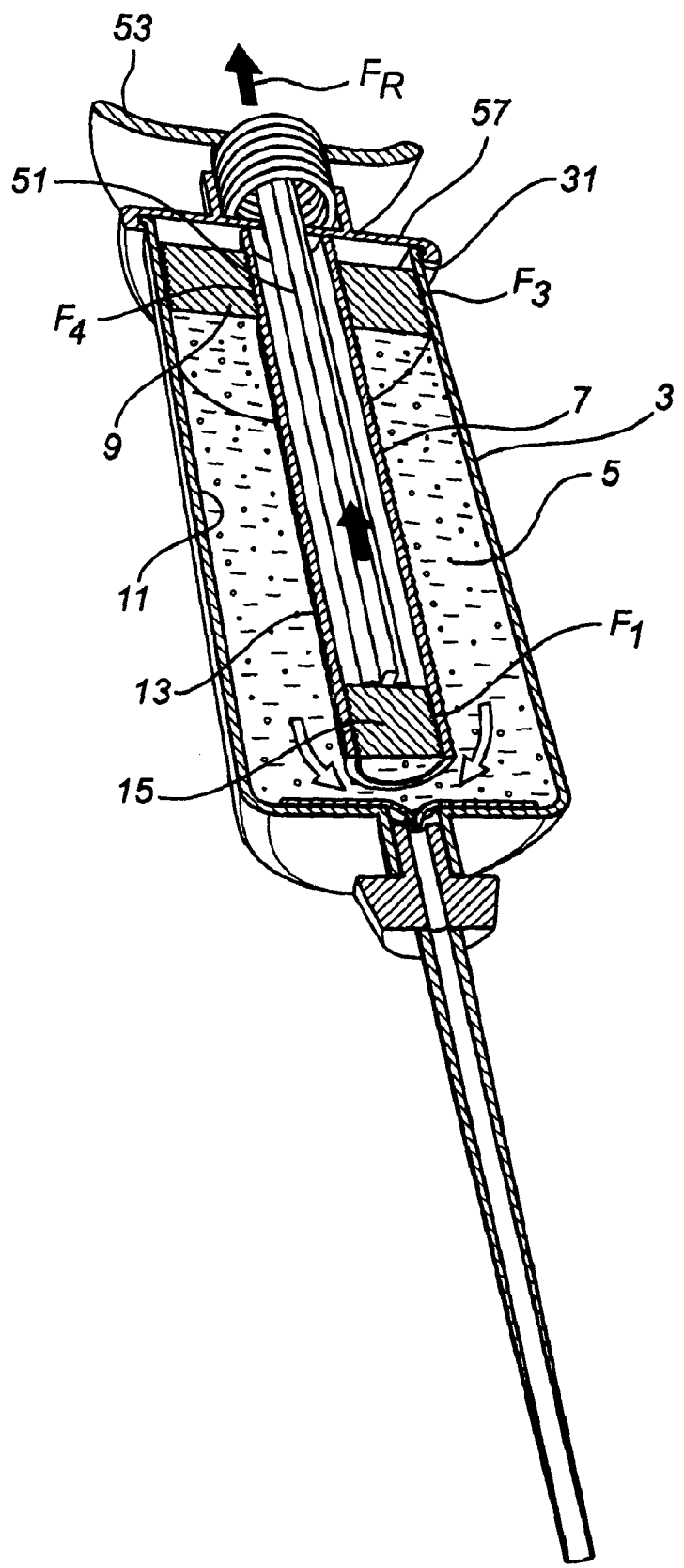
Figure 2C:
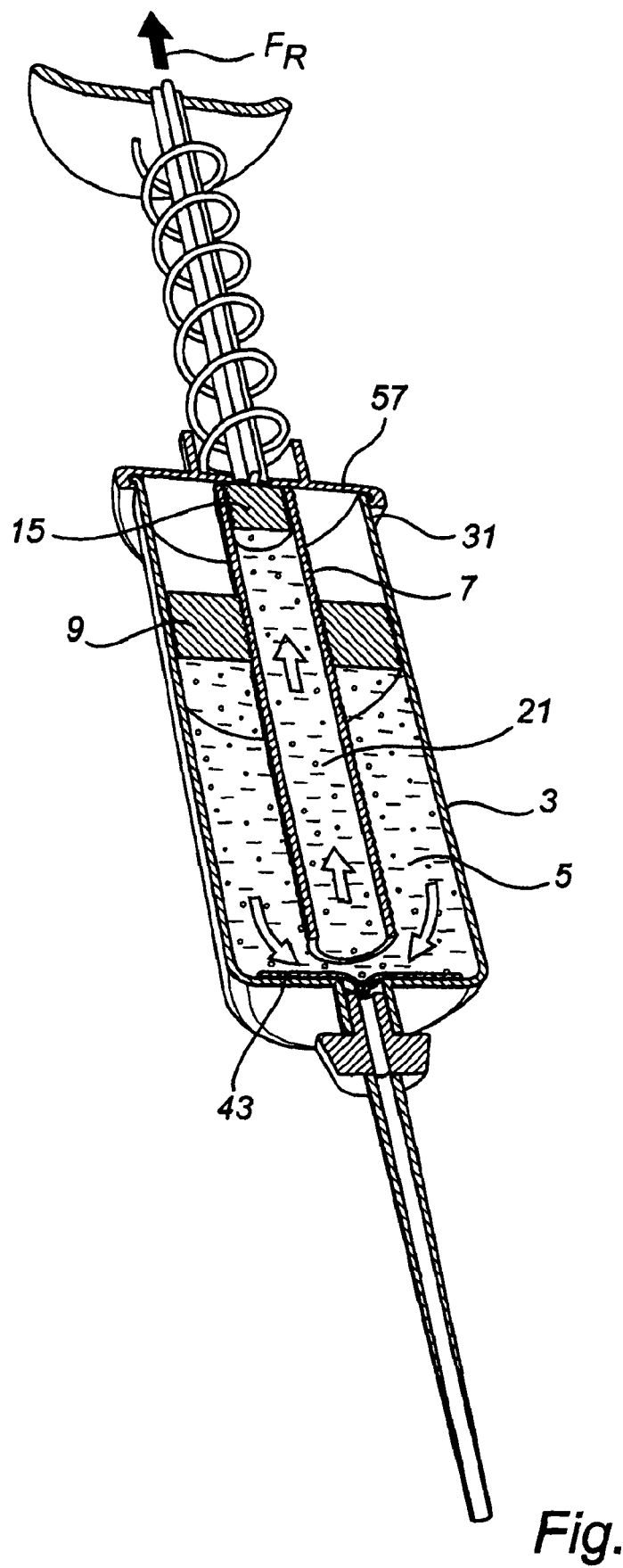

The tubular element 7 is movable in relation to the reservoir 3 between an advanced administering position (see FIGS. 1, 2a, 2d and 2e) and a retracted filling position (see FIGS. 2b and 2c). Further, the tubular element 7 is movable also in relation to the outer seal 9. At the front end 23 of the reservoir 3 is an abutment surface 43 provided to receive the end face 45 of the tubular element 7 in its advanced administering position. The abutment surface 43 is preferably made of a rubber material, such as butyl rubber. At this advanced administering position the internal space 21 of the tubular element 7 is sealed against the abutment surface 43, wherein the fluid communication between the reservoir 3 and the internal space 21 of the tubular element 7 is closed. In said advanced administering position of the tubular element the internal space 21 of the tubular element 7 is in fluid communication with the opening 25 located at the front end 45 of the reservoir 3, wherein it is possible for the fluid 5 contained inside the internal space 21 of the tubular element 7 to be delivered out from the medical pump 1 through said opening 25. When the tubular element 7 is in its retracted filling position the internal space of the tubular element 21 is in fluid communication with the rest of the reservoir 3 for enabling fluid 5 to be transferred from the reservoir 3 to said internal space 21.

It is further preferred that the outer wall 13 of the tubular element 7 is provided with an uneven surface, such as protruding means 47 in the form of splines, barbs or edges. The protruding means may be provided on a rubber coating arranged around the outer wall 13 of the tubular element. The protruding means 47 is arranged in such a way that the frictional force between the tubular element 7 and the outer seal 9 is larger when the tubular element 7 is advanced from the retracted filling position towards the advanced administering position, compared to the frictional force when retracted from the advanced administering position towards the retracted filling position 41.

The inner seal 15 provided within the tubular element 7 is preferably made of a rubber material, such as butyl rubber, for providing a sufficient sealing effect against the tubular element 7. Further, the circular circumferential surface of the inner seal 15 is preferably provided with grooves or channels 49 for increasing the sealing effect. Said inner seal 15 is attached to an elongate actuator 51 comprising a bar or shaft 55 which is movable inside the tubular element 7, wherein the shaft 55 of the actuator 51 extends to the outside of the reservoir 3. The actuator 51 is controllable from the outside of the reservoir 3 to allow the inner seal 15 to be moved between an advanced and retracted position within the tubular element 7. At the end of the shaft 55, outside the reservoir 3, the actuator 51 is provided with an control means 53, formed to be handled with a one hand grip. The shaft 55 extending between the operation means 53 and the inner seal 15 has a cross shaped cross section.

A cover 57 is arranged at the rear end 31 of the reservoir 3, containing a hole 59 preferably provided concentrically in relation to the reservoir 3 for guiding the shaft 55 of the actuator 51. Advantageously, the hole 59 in the cover 57 has a similar cross shaped form as the shaft 55, in order to provide a suitable guiding of the shaft 55. The cover 57 also act as a stop member for both the tubular element 7 and the inner seal 15, when moved from the advanced administering position to the retracted filling position. The cover 57 is preferably attached to the reservoir 3 by snap locking effect, but can also be attached with adhesive or other fastening methods.

The tubular element 7 has a length that is shorter than the distance between the abutment surface 43 and the cover 57, wherein the tubular element 7 is free to move between the abutment surface 43 and the cover 57 for enabling opening and closing of the fluid communication between the internal space 21 of the tubular element 7 and the rest of the reservoir 3. When assembled, the outer seal 9, the tubular element 7 and the inner seal 15 fit concentrically within one another along a common longitudinal axis.

A spring 61 may be arranged between the cover 57 and the control means 53 on the actuator 51, in order to transfer a retracting force to the actuator 51. This retracting force will make the movement of the inner seal 15, from the advanced position towards the retracted position, easier as well as more controlled and smooth. As an alternative, the spring 61 may be biased in a reverse manner towards its compressed state, i.e. transferring an advancing force to the actuator 51, making the forward movement easier when delivering fluid out from the medical pump 1.

Further, the abutment surface 43 preferably includes a non return valve 63 provided between the inside of reservoir 3 and the opening 25 at the front end 23. The non return valve 63 prevents the fluid 5 from mixing with air, or other fluids, when the inner seal 15 is moved from the advanced position towards the retracted position for enabling fluid 5 to transfer from the reservoir 3 into the internal space 21 of the tubular element 7. When the tubular element 7 is in the advanced administering position and the inner seal 15 is moved from the retracted position towards its advanced position, for delivering of the fluid 5 out from the medical pump 1, the non return valve 63 opens allowing fluid communication with the opening 25 at the front end 23 of the reservoir 3. The non-return valve 63 is suitably formed as a slit in the abutment surface, wherein two flaps are provided for opening and closing the fluid communication between the reservoir 3 and the opening 25. When the inner seal is moved from the retracted position towards the advanced position for delivering of fluid 5 from the medical pump 1, the fluid 5 forces the flaps to separate, thereby opening the non-return valve 63.

In order to use the medical pump 1, the tubular element 7 and the inner seal 15 is first located in the advanced position as seen in FIG. 2a. At this point all the fluid 5 remains within the reservoir 3, since the internal space 21 of the tubular element 7 is sealed against the abutment surface 43 and thereby closed from fluid communication with the reservoir 3.

The medical pump 1 is preferably delivered in this condition, wherein a safety sealing (not shown) is arranged to keep the tubular element 7 and the inner seal 15 at the advanced position. Advantageously, the safety seal is provided to secure the advanced position of the actuator 51 relative to the medical pump 1. The medical pump 1 is preferably disposable for one time use, wherein the safety seal indicates whether the medical pump has been used or not. The safety seal is suitably broken immediately before administration of medical fluid 5.

In FIG. 2b, a retracting force $F_R$ is applied to the control means 53 on the actuator 51. The retracting movement of the actuator 51, and thereby the inner seal 15, creates a frictional force $F_1$ between the inner seal 15 and the tubular element 7. This frictional force $F_1$ cause the tubular element 7 to be displaced in a retracting direction towards the cover 57 at the rear end 31 of the reservoir 3. When the tubular element 7 is moved from the advanced administering position to the retracted filling position fluid communication into the tubular element 7 is made possible as soon as the inner seal 15 is further retracted to create the internal space 21 of the tubular element 7. Additionally, when the tubular element 7 is moved towards the retracted filling position, a frictional force $F_3$ is created between the outer seal 9 and the inner wall 11 of the reservoir 3, and a frictional force $F_4$ is created between the outer seal 9 and the outer wall 13 of the tubular element 7. The frictional forces $F_3$ and $F_4$ are dimensioned to essentially retain the position of the outer seal 9 in relation to the reservoir 3 during the movement of the tubular element 7, but allowing the tubular element 7 to be displaced relative the outer seal 9. To obtain this the relation between the frictional forces is $F_3>F_4$. Hence, the outer seal 9 is retained in position to have the same level as the fluid 5 within the reservoir 3. Furthermore, in order to also enable the tubular element 7 to be lifted due to the frictional force $F_1$ between the inner seal 15 and the tubular element, while allowing the outer seal 9 to remain in position relative to the reservoir 3 but allow movement relative to the tubular element 7, the relation between the frictional forces is $F_1>F_3>F_4$.

After the tubular element 7 has been retracted to a position where it contacts the cover 57 and is thus prevented from further backwards movement, continued retraction of the inner seal 15 creates a reduced pressure inside the tubular element 7. This reduced pressure transfers or draws fluid 5 from the reservoir 3 into the internal space 21 of the tubular element 7. As shown in FIG. 2c the fluid 5 will pass through the gap between the tubular element 7 and the abutment surface 43 into the internal space 21 of the tubular element 7. The retraction of the inner seal 15 is limited by the cover 57 at the rear end 31 of the reservoir 3. When the inner seal 15 is retracted completely to the retracted position and abuts against the cover 57, about 3 ml of fluid will be contained in the internal space 21 of the tubular element 7.

When fluid 5 is transferred from the reservoir 3 into the internal space 21 of the tubular element 7, the outer seal 9 is following the reduced level of fluid 5 in the part of the reservoir 3 outside the tubular element 7. The reduced pressure in the reservoir 3 that arise when the fluid 5 is transferred from the reservoir 3 into the tubular element 7 creates a suction force, which makes the outer seal 9 follow the level of fluid 5 in the reservoir 3. By moving the outer seal 9 the level of fluid 5 outside the tubular element 7 is decreased without introducing any air into the fluid 5. At the side of the outer seal 9 opposite to the fluid air is introduced either through an opening (not shown) in the cover 57 or underneath the cover 57, in order to equalize the pressure surrounding the outer seal 9.

Figure 2D:
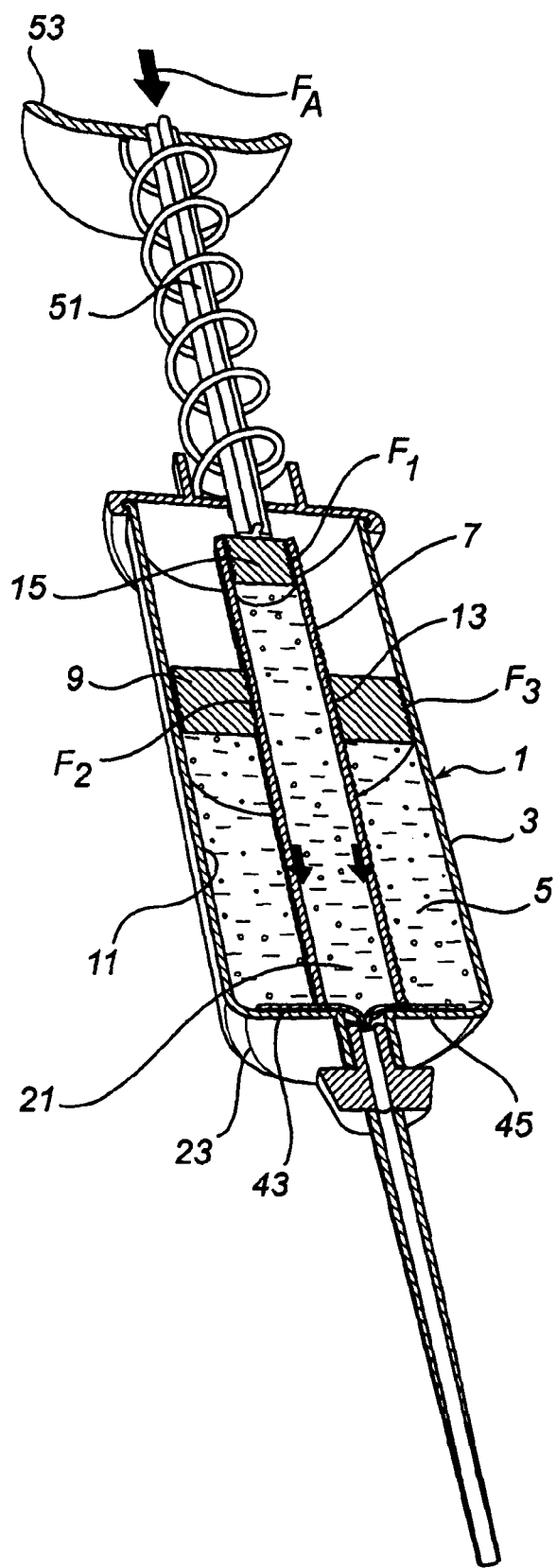

When the internal space 21 of the tubular element 7 is filled, an advancing force $F_A$ is applied to the operation means 53 of the actuator 51 for delivering out of the medical pump 1 the fluid 5 contained inside the internal space 21. The advancing movement of the actuator 51 as seen in FIG. 2d, and thereby the inner seal 15, creates a frictional force $F_1$ between the inner seal 15 and the tubular element 7 in the same way as when the inner seal 15 was retracted. This frictional force $F_1$ cause the tubular element 7 to be displaced in a advancing direction towards the abutment surface 43 at the front end 23 of the reservoir 3. When the tubular element 7 is moved from the retracted filling position to the advanced administering position the fluid communication is closed between the reservoir 3 and the internal space 21 of the tubular element 7 by the sealing effect created between the end face 45 of the tubular element 7 and the abutment surface 43. Additionally, when the tubular element 7 is moved towards the advanced administering position, a frictional force $F_3$ is created between the outer seal 9 and the inner wall 11 of the reservoir 3, and a frictional force $F_2$ is created between the outer seal 9 and the outer wall 13 of the tubular element 7. The frictional forces $F_3$ and $F_2$ are dimensioned to permit the outer seal 9 to at least partially follow the translation of the tubular element 7. To obtain this is the relation between the frictional forces is $F_2>F_3$. Thus, it is to be noted that in this case the frictional force between the outer seal 9 and the outer wall 13 of the tubular element 7 is different during advancement ($F_2$) and retraction ($F_4$) of the tubular element, wherein $F_2>F_4$. This difference can be achieved by the previously discussed uneven rubber surface on the outer wall 13. The movement of the outer seal 9, following at least partially the movement of the tubular element 7, relatively to the reservoir 3 creates a pressure in the fluid 5, and in case the pressure together with the frictional force $F_3$ generates a force, directed upwardly to the outer seal 9, larger than the frictional force $F_2$, the movement of the outer seal 9 is discontinued. For a person skilled in the art is it obvious that the medical pump according to the invention can be arranged with an outer seal 9 that essentially retains the position in relation to the reservoir 3 during the movement of the tubular element 7 towards the advanced administering position. To obtain this the relation between the frictional forces would be $F_3>F_2$.

Figure 2E:
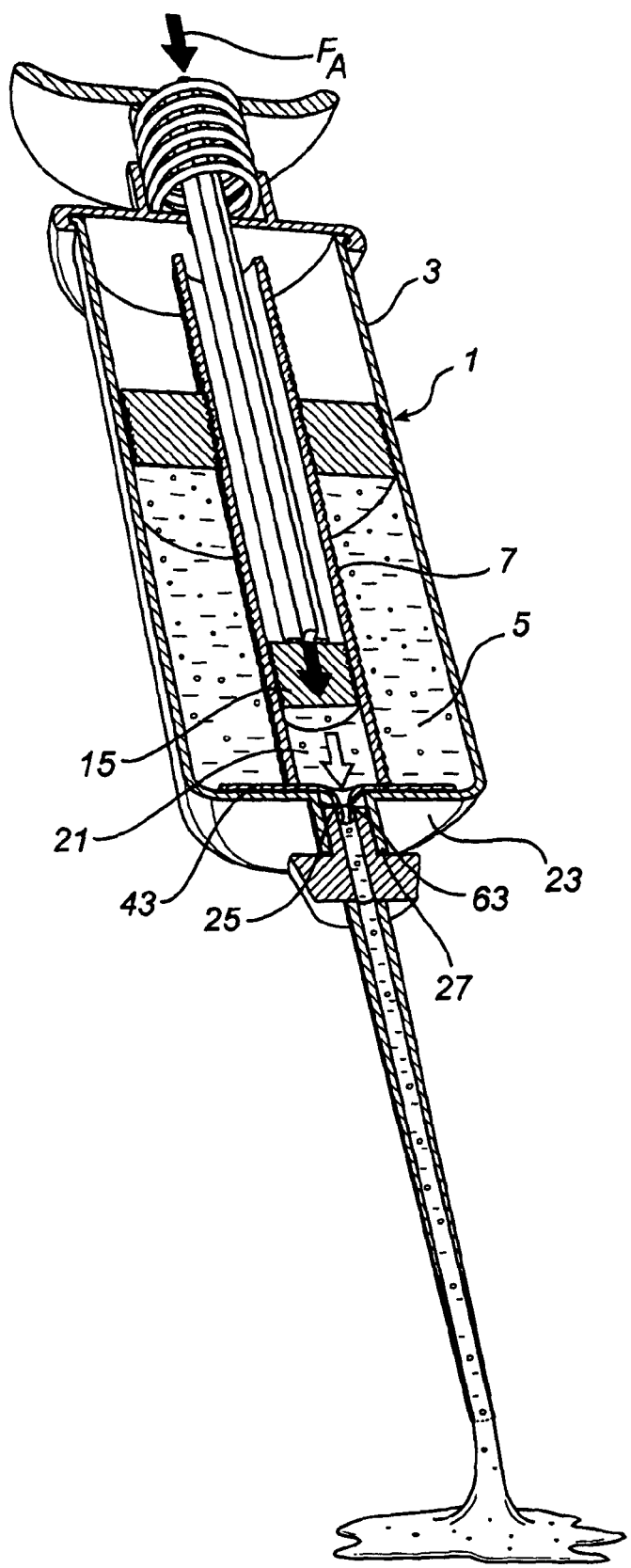

After the tubular element 7 is advanced to a position where it contacts the abutment surface 43, further advancing movement of the inner seal 15 forces the fluid 5 from the internal space out through the opening 25 at the front end 23 of the reservoir 3, as seen in FIG. 2e. The inner seal 15 is advanced until it bottoms the abutment surface 43 at the front end 23 of the reservoir 3, wherein the inside of the tubular element 7 is drained from fluid 5 as the internal space 21 diminishes. In the embodiment with a non return valve 63 provided between the reservoir 3 and the opening 25, the fluid 5 forces the non return valve 63 to open, and thereby a fluid communication with the tubular end portion 27 is opened.

When the fluid 5 contained within the internal space 21 of the tubular element 7 is delivered out from the medical pump 1, the internal space 21 may be recreated and refilled by repeating the procedure described. This procedure may be repeated until essentially all the fluid 5 has been transferred into and delivered out from the tubular element 7.

In order to assemble the medical pump 1, a reservoir 3 is first provided (as seen in FIG. 3a), wherein the outer seal 9 is introduced into the reservoir 3 (as seen in FIG. 3b). The circumferential outer surface of the outer seal 9 abuts against the inner wall 11 of the reservoir 3 to provide a sealing effect. After introduction of the outer seal 9, the fluid 5 is introduced into the reservoir through the hole 35 in the outer seal 9, as seen in FIG. 3c. The complete volume delimited by the outer seal 9 is essentially filled up with fluid 5. When the fluid 5 is introduced, the tubular element 7 comprising the inner seal 15 is introduced through the hole 35 in the outer seal 9 (as seen in FIG. 3d), wherein the volume of fluid 5 contained in the reservoir 3 is sealed from communication with the environment (as seen in FIG. 3e).

Preferably, the tubular element 7 comprising the inner seal 15 is introduced together with the elongate actuator 51 and the cover 57 as an pre-assembled unit.

It is obvious for a person skilled in the art that the same result is achieved by introducing the fluid 5 into the reservoir 3 before the introduction of the outer seal 9. In the case where the fluid 5 is introduced before the outer seal 9, the outer seal 9 is preferably introduced in the reservoir 3 together with the tubular element 7 comprising the inner seal 15, the elongate actuator 51 and the cover 57 as an pre-assembled unit.

Preferably, the assembling of the medical pump 1 is executed in a environment free from air, such as a vacuum area, for avoiding introduction of air into the fluid enclosing portion in the reservoir 3. When the medical pump 1 is assembled, the medical pump 1 is preferably encompassed in a sterilized package to avoid contamination.

The invention claimed is:

1. A medical pump, comprising:
a reservoir having a fluid enclosing portion;
a tubular element, the inside of which is arrangeable in fluid communication with the fluid enclosing portion for allowing fluid to pass into the tubular element;
an inner seal movable inside the tubular element between an advanced and a retracted position, wherein the inner seal is retractable from the advanced position to enable the fluid to be transferred from the fluid enclosing portion into an internal space defined by the tubular element and the retracted inner seal, and wherein the inner seal is advanceable from the retracted position for delivering out of the pump fluid present in said internal space;
wherein said fluid enclosing portion contains a volume of fluid sealed from communication with air and the fluid enclosing portion is adapted to reduce in volume essentially to the same extent as any volume of fluid transferred into said internal space of the tubular element;
wherein said fluid enclosing portion comprises a outer seal which is movable inside the reservoir and which defines a delimitation of the fluid contained in the fluid enclosing portion, the outer seal being arranged to move relative to the tubular element when the inner seal is retracted from said advanced position;
wherein the tubular element is located inside the reservoir, wherein the outer seal extends from an inner surface of the reservoir to an outer surface of the tubular element;
wherein the tubular element is movable between an advanced administering position and a retracted filling position, wherein the outer seal is adapted to move relative to the tubular element when the tubular element is retracted from said administering position;
wherein mutually contacting surfaces of the tubular element and the outer seal provide a frictional force $F_2$ against advancing movement of the tubular element towards its administering position, and wherein mutually contacting surfaces of the outer seal and the reservoir provide a frictional force $F_3$ which is smaller than the frictional force $F_2$, wherein the outer seal is advanced together with the tubular element during advancement of the tubular element towards its administering position; and wherein the reservoir has an outlet covered by an abutment surface that obstructs a fluid flow from the outlet and into the reservoir.

2. The medical pump as claimed in claim 1, wherein mutually contacting surfaces of the inner seal and the tubular element provide a frictional force $F_1$, wherein the tubular element is adapted to be retracted from the administering position by application of a retracting force on the inner seal.

3. The medical pump as claimed in claim 2, wherein the tubular element is adapted to be advanced from the filling position by application of an advancing force on the inner seal.

4. The medical pump as claimed in claim 1, wherein mutually contacting surfaces of the tubular element and the outer seal provide a frictional force $F_4$ against retracting movement of the tubular element towards its filling position, the frictional force $F_3$ being larger than the frictional force $F_4$.

5. The medical pump as claimed in claim 1, wherein
mutually contacting surfaces of the inner seal and the tubular element provide a frictional force $F_1$;
mutually contacting surfaces of the tubular element and the outer seal provide a frictional force $F_4$ against retracting movement of the tubular element towards its filling position; and
wherein said frictional forces satisfy the relationship $F_1 > F_2 > F_3 > F_4$.

6. The medical pump as claimed in claim 1, wherein the abutment surface permits fluid delivery out of the pump, wherein, in said administering position, an end portion of the tubular element abuts said abutment surface in such manner that said internal space of the tubular element is in communication with said outlet.

7. The medical pump as claimed in claim 6, wherein the abutment surface prevents fluid from flowing between the interior of the tubular element and the reservoir when the tubular element is in said administering position.

8. The medical pump as claimed in claim 7, wherein the abutment surface includes a non-return valve which allows fluid to flow out from the pump through said outlet but which prevents fluid to enter the pump through said outlet.

9. The medical pump as claimed in claim 8, wherein the retracted filling position of the tubular element is determined by an end member of the reservoir preventing further retraction of the tubular element.

10. The medical pump as claimed in claim 1, wherein said inner seal is connected to an elongate actuator movable inside the tubular element, the actuator being controllable from the outside of the reservoir,
wherein, when the inner seal is retracted from the advanced position due to a retracting force acting on the actuator, the tubular element is retracted to its filling position due to friction against the inner seal, and
wherein the inner seal is adapted to overcome the friction and move relative to the tubular element when the tubular element is at its filling position and the actuator is subjected to a retraction force.

11. The medical pump as claimed in claim 10, wherein a spring is provided and biased to exert a force on the elongate actuator in the longitudinal direction of the actuator.

12. The medical pump as claimed in claim 1, wherein the pump is provided as a package in which the reservoir is pre-filled with a medical fluid in the form of a gel having a viscosity above 1000 mPa*s.

13. A method of delivering a medical fluid, comprising:
providing a medical pump comprising a reservoir having a fluid enclosing portion and a tubular element, the inside of which is arrangeable in fluid communication with the fluid enclosing portion;

providing the fluid enclosing portion with an outer seal which is movable inside the reservoir and which defines a delimitation of the fluid contained in the fluid enclosing portion to prevent the fluid from mixing with air;

reducing the volume of the fluid enclosing portion and moving the outer seal relative to the tubular element by transferring a portion of said fluid from the fluid enclosing portion into an internal space of the tubular element, wherein the volume of the fluid enclosing portion is reduced with essentially the same volume as the volume of fluid transferred into the internal space of the tubular element;

delivering out from the pump the transferred fluid contained in the internal space of the tubular element;

moving the outer seal relatively to the tubular element by moving the tubular element from an advanced administering position towards a retracted filling position;

retaining the position of the outer seal relatively to the reservoir when the tubular element is moved from the advanced administering position towards the retracted filling position;

advancing the outer seal together with the retracted tubular element by moving the retracted tubular element towards the advanced administering position; and covering an outlet of the reservoir with an abutment surface that obstructs a fluid flow from the outlet and into the reservoir.

14. The method according to claim 13 further comprising:
repeating the preceding steps for further delivering of fluid from the pump.

15. The method according to claim 13, wherein the act of moving the outer seal comprises establishing a negative pressure inside the tubular element, which negative pressure forces the fluid and the outer seal to be moved.

16. The method according to claim 15, wherein the act of providing a pump comprises providing a movable inner seal inside the tubular element, wherein the act of establishing the negative pressure comprises moving said inner seal inside the tubular element from an advanced position to a retracted position, thereby transferring a portion of said fluid from the reservoir into the internal space of the tubular element.

17. The method according to claim 16, wherein the act of delivering fluid out from the pump comprises moving said inner seal from the retracted position to the advanced position, thereby delivering out from the pump the transferred fluid contained in the internal space of the tubular element.

18. A medical pump, comprising:
a reservoir having a fluid enclosing portion;
a tubular element, the inside of which is arrangeable in fluid communication with the fluid enclosing portion for allowing fluid to pass into the tubular element;
an inner seal movable inside the tubular element between an advanced and a retracted position, wherein the inner seal is retractable from the advanced position to enable the fluid to be transferred from the fluid enclosing portion into an internal space defined by the tubular element and the retracted inner seal, and wherein the inner seal is advanceable from the retracted position for delivering out of the pump fluid present in said internal space;
wherein said fluid enclosing portion contains a volume of fluid sealed from communication with air and the fluid enclosing portion is adapted to reduce in volume essentially to the same extent as any volume of fluid transferred into said internal space of the tubular element;
wherein said fluid enclosing portion comprises a outer seal which is movable inside the reservoir and which defines a delimitation of the fluid contained in the fluid enclosing portion, the outer seal being arranged to move relative to the tubular element when the inner seal is retracted from said advanced position;
wherein the tubular element is located inside the reservoir, wherein the outer seal extends from an inner surface of the reservoir to an outer surface of the tubular element;
wherein the tubular element is movable between an advanced administering position and a retracted filling position, wherein the outer seal is adapted to move relative to the tubular element when the tubular element is retracted from said administering position;
wherein mutually contacting surfaces of the outer seal and the reservoir provide a frictional force $F_3$, and wherein mutually contacting surfaces of the tubular element and the outer seal provide a frictional force $F_4$ against retracting movement of the tubular element towards its filling position, the frictional force $F_3$ being larger than the frictional force $F_4$; and
wherein the reservoir has an outlet covered by an abutment surface that obstructs a fluid flow from the outlet and into the reservoir.

19. A medical pump, comprising:
a reservoir having a fluid enclosing portion;
a tubular element, the inside of which is arrangeable in fluid communication with the fluid enclosing portion for allowing fluid to pass into the tubular element;
an inner seal movable inside the tubular element between an advanced and a retracted position, wherein the inner seal is retractable from the advanced position to enable the fluid to be transferred from the fluid enclosing portion into an internal space defined by the tubular element and the retracted inner seal, and wherein the inner seal is advanceable from the retracted position for delivering out of the pump fluid present in said internal space;
wherein said fluid enclosing portion contains a volume of fluid sealed from communication with air and the fluid enclosing portion is adapted to reduce in volume essentially to the same extent as any volume of fluid transferred into said internal space of the tubular element;
wherein said fluid enclosing portion comprises a outer seal which is movable inside the reservoir and which defines a delimitation of the fluid contained in the fluid enclosing portion, the outer seal being arranged to move relative to the tubular element when the inner seal is retracted from said advanced position;
wherein the tubular element is located inside the reservoir, wherein the outer seal extends from an inner surface of the reservoir to an outer surface of the tubular element;
wherein the tubular element is movable between an advanced administering position and a retracted filling position, wherein the outer seal is adapted to move relative to the tubular element when the tubular element is retracted from said administering position;
wherein mutually contacting surfaces of the inner seal and the tubular element provide a frictional force $F_1$;
wherein mutually contacting surfaces of the tubular element and the outer seal provide a frictional force $F_2$ against advancing movement of the tubular element towards its administering position;

wherein mutually contacting surfaces of the outer seal and the reservoir provide a frictional force $F_3$;

wherein mutually contacting surfaces of the tubular element and the outer seal provide a frictional force $F_4$ against retracting movement of the tubular element towards its filling position;

wherein said frictional forces satisfy the relationship $F_1 > F_2 > F_3 > F_4$; and wherein the reservoir has an outlet covered by an abutment surface that obstructs a fluid flow from the outlet and into the reservoir.

20. A method of delivering a medical fluid, comprising:

providing a medical pump including
- a reservoir having a fluid enclosing portion, and
- a tubular element that is moveable relative to the reservoir between an administering position and a filling position;

providing the fluid enclosing portion with an outer seal which is movable inside the reservoir and which defines a delimitation of the fluid contained in the fluid enclosing portion to prevent the fluid from mixing with air;

providing an inner seal inside the tubular element for movement between an advanced position and a retracted position, wherein the inner seal is retractable from the advanced position to enable the fluid to be transferred from the fluid enclosing portion into an internal space defined by the tubular element and the retracted inner seal;

reducing the volume of the fluid enclosing portion and moving the outer seal relative to the tubular element by transferring a portion of said fluid from the fluid enclosing portion into the internal space of the tubular element, wherein the volume of the fluid enclosing portion is reduced with essentially the same volume as the volume of fluid transferred into the internal space of the tubular element;

covering an outlet of the reservoir with an abutment surface that obstructs a fluid flow from the outlet and into the reservoir;

delivering out from the pump the transferred fluid contained in the internal space of the tubular element; and wherein mutually contacting surfaces of the tubular element and the outer seal provide a frictional force $F_2$ against advancing movement of the tubular element towards its administering position, and wherein mutually contacting surfaces of the outer seal and the reservoir provide a frictional force $F_3$ which is smaller than the frictional force $F_2$, wherein the outer seal is advanced together with the tubular element during advancement of the tubular element towards its administering position.

21. A method of delivering a medical fluid, comprising:

providing a medical pump including
- a reservoir having a fluid enclosing portion, and
- a tubular element that is moveable relative to the reservoir between an administering position and a filling position;

providing the fluid enclosing portion with an outer seal which is movable inside the reservoir and which defines a delimitation of the fluid contained in the fluid enclosing portion to prevent the fluid from mixing with air;

providing an inner seal inside the tubular element for movement between an advanced position and a retracted position, wherein the inner seal is retractable from the advanced position to enable the fluid to be transferred from the fluid enclosing portion into an internal space defined by the tubular element and the retracted inner seal;

reducing the volume of the fluid enclosing portion and moving the outer seal relative to the tubular element by transferring a portion of said fluid from the fluid enclosing portion into the internal space of the tubular element, wherein the volume of the fluid enclosing portion is reduced with essentially the same volume as the volume of fluid transferred into the internal space of the tubular element;

covering an outlet of the reservoir with an abutment surface that obstructs a fluid flow from the outlet and into the reservoir;

delivering out from the pump the transferred fluid contained in the internal space of the tubular element; and wherein mutually contacting surfaces of the outer seal and the reservoir provide a frictional force $F_3$, and wherein mutually contacting surfaces of the tubular element and the outer seal provide a frictional force $F_4$ against retracting movement of the tubular element towards its filling position, the frictional force $F_3$ being larger than the frictional force $F_4$.

22. A method of delivering a medical fluid, comprising:

providing a medical pump including
- a reservoir having a fluid enclosing portion, and
- a tubular element that is moveable relative to the reservoir between an administering position and a filling position;

providing the fluid enclosing portion with an outer seal which is movable inside the reservoir and which defines a delimitation of the fluid contained in the fluid enclosing portion to prevent the fluid from mixing with air;

providing an inner seal inside the tubular element for movement between an advanced position and a retracted position, wherein the inner seal is retractable from the advanced position to enable the fluid to be transferred from the fluid enclosing portion into an internal space defined by the tubular element and the retracted inner seal;

reducing the volume of the fluid enclosing portion and moving the outer seal relative to the tubular element by transferring a portion of said fluid from the fluid enclosing portion into the internal space of the tubular element, wherein the volume of the fluid enclosing portion is reduced with essentially the same volume as the volume of fluid transferred into the internal space of the tubular element;

covering an outlet of the reservoir with an abutment surface that obstructs a fluid flow from the outlet and into the reservoir;

delivering out from the pump the transferred fluid contained in the internal space of the tubular element; and wherein mutually contacting surfaces of the inner seal and the tubular element provide a frictional force $F_1$;

wherein mutually contacting surfaces of the tubular element and the outer seal provide a frictional force $F_2$ against advancing movement of the tubular element towards its administering position;

wherein mutually contacting surfaces of the outer seal and the reservoir provide a frictional force $F_3$;

wherein mutually contacting surfaces of the tubular element and the outer seal provide a frictional force $F_4$ against retracting movement of the tubular element towards its filling position; and wherein said frictional forces satisfy the relationship $F_1 > F_2 > F_3 > F_4$.

* * * * *